United States Patent
Gao et al.

(10) Patent No.: US 9,645,114 B2
(45) Date of Patent: May 9, 2017

(54) SINGLE MAGNET FLUID DENSITOMETER

(75) Inventors: Li Gao, Katy, TX (US); Michael T. Pelletier, Houston, TX (US); Mark A. Proett, Missouri City, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 14/391,612

(22) PCT Filed: May 3, 2012

(86) PCT No.: PCT/US2012/036372
§ 371 (c)(1),
(2), (4) Date: Oct. 9, 2014

(87) PCT Pub. No.: WO2013/165428
PCT Pub. Date: Nov. 7, 2013

(65) Prior Publication Data
US 2015/0070000 A1    Mar. 12, 2015

(51) Int. Cl.
*G01V 3/00* (2006.01)
*E21B 49/00* (2006.01)
(Continued)

(52) U.S. Cl.
CPC ............ *G01N 27/74* (2013.01); *E21B 47/06* (2013.01); *E21B 47/102* (2013.01); *E21B 49/00* (2013.01);
(Continued)

(58) Field of Classification Search
CPC ........ G01N 27/74; G01N 9/002; G01N 11/16; G01N 2009/006; E21B 49/00; E21B 47/06; E21B 47/102; E21B 2049/085
(Continued)

(56) References Cited

U.S. PATENT DOCUMENTS 2,156,052 A * 4/1939 Cooper .................. G01V 1/52
                                                      181/104
4,679,947 A    7/1987 Miller et al.
(Continued)

FOREIGN PATENT DOCUMENTS

DE          2828016 A1    1/1980
DE     102004023600 A1   12/2005

OTHER PUBLICATIONS

International Search Report and The Written Opinion of the International Searching Authority, or the Declaration, Jul. 13, 2012, PCT/US2012/036372, 10 pages, International Searching Authority, U.S.
Extended European Search Report, Sep. 1, 2015, EP 12875861.2, 7 pages.
Extended European Search Report, Jul. 14, 2016, 16167042, 7 pages.

*Primary Examiner* — Farhana Hoque
(74) *Attorney, Agent, or Firm* — Haynes and Boone, LLP

(57) ABSTRACT

An instrument for determining fluid properties is provided. The instrument (300) includes a tube (304) receiving the fluid, a single magnet (302) attached to the tube, and a single coil (306) wound around the single magnet. The single coil is coupled to a pulse current source (312) and receives a pulse current that creates a magnetic field in the single coil, the created magnetic field interacting with the single magnet to drive the tube to vibrate. The instrument further includes a detector (306) coupled to the tube, wherein the detector is coupled to measurement circuitry (310) and detects properties of the tube as it vibrates, and the measurement circuitry determines the fluid properties based on the detected properties. The instrument also includes a housing (314) enclosing the tube, the single magnet, and the single coil wound around the single magnet.

22 Claims, 10 Drawing Sheets

(51) Int. Cl.
*G01N 27/74* (2006.01)
*E21B 47/06* (2012.01)
*E21B 47/10* (2012.01)
*G01N 9/00* (2006.01)
*G01N 11/16* (2006.01)
*G01N 33/28* (2006.01)
*E21B 49/08* (2006.01)

(52) U.S. Cl.
CPC ............ *E21B 49/08* (2013.01); *G01N 9/002* (2013.01); *G01N 11/16* (2013.01); *G01N 33/2823* (2013.01); *E21B 2049/085* (2013.01); *G01N 2009/006* (2013.01)

(58) Field of Classification Search
USPC .............................. 324/204, 338; 73/152.05
See application file for complete search history.

(56) References Cited

U.S. PATENT DOCUMENTS

| | | | |
|---|---|---|---|
| 4,949,583 | A | 8/1990 | Lang et al. |
| 4,984,472 | A | 1/1991 | Dahlin |
| 5,533,381 | A | 7/1996 | Seale |
| 6,543,281 | B2 | 4/2003 | Pelletier et al. |
| 6,688,176 | B2 | 2/2004 | Storm, Jr. et al. |
| 6,912,904 | B2 | 7/2005 | Storm, Jr. et al. |
| 2004/0123645 | A1 | 7/2004 | Storm, Jr. et al. |
| 2010/0268469 | A1* | 10/2010 | Harrison ............... G01N 9/002 702/12 |
| 2011/0167910 | A1* | 7/2011 | Storm ..................... G01F 1/74 73/32 A |

\* cited by examiner

SINGLE MAGNET FLUID DENSITOMETER

The present application is a U.S. National Stage patent application of International Patent Application No. PCT/US2012/036372, filed on May 3, 2012, the benefit of which is claimed and the disclosure of which is incorporated herein by reference in its entirety.

BACKGROUND

1. Technical Field

Embodiments disclosed herein generally relate to the measurement of fluid properties. In particular, the disclosed embodiments are related to determining a density of a fluid using a single magnet fluid densitometer.

2. Description of Related Art

There are many instances in industrial processes and controls for handling flowing fluids where the density of the moving fluid has to be determined accurately. One particular application is in the identification of reservoir fluids flowing in a well such as in a pumpout wireline formation tester (PWFT) or logging while drilling formation tester (LWDFT) used to collect reservoir fluid samples in a well drilled for hydrocarbon exploration. The in-situ determination of fluid density under reservoir conditions is of vital importance in formation evaluation. Water often co-exists with gaseous hydrocarbons and crude oil in some common geologic formations. As such, a mixture of water, gaseous hydrocarbons, and liquid hydrocarbons is often produced by a working oil well, and the mixture is ultimately separated at a downstream location. It is often desirable to determine the amount of oil that is produced in a stream flowing from a formation. Because the amount of oil produced in the stream will influence the density of the fluid, measuring the density of the fluid can provide a reasonable estimation as to the amount of oil in the fluid.

One example of a densitometer that can be used to measure the density of an unknown process fluid is a Coriolis mass flowmeter, such as disclosed in U.S. Pat. No. 4,491,025, issued to Smith et al. A Coriolis mass flowmeter may contain two parallel conduits, each typically being a U-shaped flow tube wherein each flow tube is driven such that it oscillates about an axis causing each tube to twist about a torsional axis to produce a slight deformation and deflection of the conduit proportional to the mass flow rate of the fluid. This deformation is normally measured as a small difference between the deflection at the inlet ends of the conduits compared to the deflection at the outlet ends. Both tubes are oppositely driven such that each tube behaves as a separate tine of a tuning fork and thereby cancels any undesirable vibrations that might otherwise mask the Coriolis forces. The resonant frequency at which each flow tube oscillates depends upon its total mass, i.e. the mass of the empty tube itself plus the mass of the fluid flowing therethrough. Inasmuch as the total mass will vary as the density of the fluid flowing through the tube varies, the resonant frequency will likewise vary with any changes in density.

Another example of a densitometer is discussed in U.S. Pat. No. 4,491,009, issued to Reusch, wherein the density of an unknown fluid flowing through an oscillating flow tube is proportional to the square of the period at which the tube resonates. A further exemplary densitometer is disclosed in U.S. Pat. No. 6,378,364, by Pelletier et al., which is assigned to the same assignee as the present disclosure. Therein, a measurement device compares vibration frequencies from a sample cavity and a reference cavity to determine desired fluid properties.

However, due to the limited space in downhole applications, in most of the densitometers described above, the transmitter or driver is often located in close proximity to the receiver and may cause interference between the two components. The interference may distort the signal picked up on the receiver and cause difficulty in accurately recognizing the vibratory response of the flow tube. Thus, many of the prior art methods have used multiple flow tubes to create a reference point to cancel out external interference.

Consequently, there is a need for a high-accuracy densitometer which is capable of operation under the high temperature, pressure, shock and vibration conditions encountered in a wellbore. There is also a need for a densitometer which allows for a greater ease of construction and improved sensitivity over existing densitometers. Furthermore, there is a need for a device that not only is capable of determining a density of a fluid, but can also simultaneously determine other properties of a fluid, such as a fluid pressure and a fluid viscosity.

BRIEF SUMMARY

Consistent with some embodiments, an instrument for measuring fluid properties is provided. The instrument includes a tube that receives a sample of the fluid, a single magnet coupled to the tube, at least one coil wound around the single magnet, and a testing module coupled to the at least one coil wound around the single magnet.

Consistent with further embodiments, there is also provided an instrument for determining fluid properties. The instrument includes a tube receiving the fluid, a single magnet attached to the tube, and at least one coil wound around the single magnet. The at least one coil is coupled to a pulse current source and receives a pulse current that creates a magnetic field in the at least one coil, the created magnetic field interacting with the single magnet to drive the tube to vibrate. The instrument further includes a detector coupled to the tube, wherein the detector is coupled to measurement circuitry and detects properties of the tube as it vibrates, and the measurement circuitry determines the fluid properties based on the detected properties.

These and other embodiments will be described in further detail below, with reference to the following drawings.

BRIEF DESCRIPTION OF THE DRAWINGS

Wherever possible, the same reference numbers are used throughout the drawings to refer to the same or like elements.

DETAILED DESCRIPTION

Figure 1:
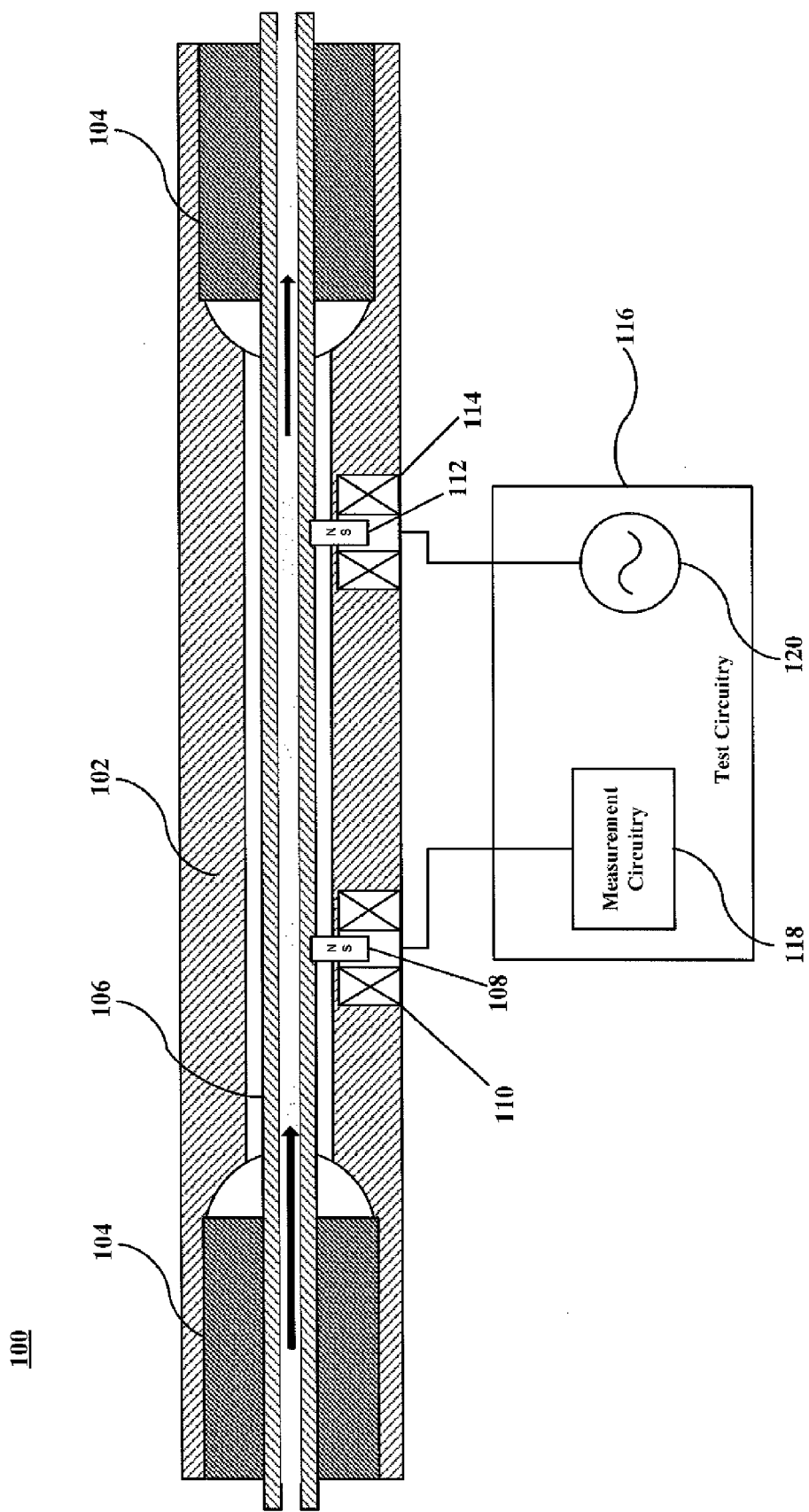
FIG. 1 is a device for measuring a density of a fluid.

FIG. 1 is a device for measuring a density of a fluid. As shown in FIG. 1, device 100 includes a rigid housing 102, two bulkheads 104, a single flow tube 106, a first magnet 108 and a first coil 110 wound around first magnet 108, a second magnet 112 and a second coil 114 wound around second magnet 112, and test circuitry 116 which includes measurement circuitry 118 and current source 120. The rigid housing 102 surrounds and protects a volume through which flow tube 106 passes and reduces the response to vibrations not associated with particular vibratory modes of flow tube 106. Bulkheads 104 seal the volume and secure flow tube 106 within that volume. The volume preferably contains air, a vacuum or a relatively inert gas such as nitrogen or argon. If gasses are used, then they are preferably at atmospheric pressure when the device is at room temperature.

Rigid housing 102, bulkheads 104, and flow tube 106 are preferably made from material in a configuration that can withstand pressures of more than 20,000 psi (pounds per square inch) at temperatures of 250° C. or more. Two examples of suitable materials are Titanium and Hastaloy-HA276C. Preferably, bulkheads 104 and flow tube 106 are constructed from the same piece of material, with bulkheads 104 being regions of larger diameter on either end of flow tube 106. Alternatively, flow tube 106 may be welded to bulkheads 104, or otherwise attached. Preferably, rigid housing 102, bulkheads 104, and flow tube 106 are constructed from the same material in order to alleviate thermally induced stresses when the system is in thermal equilibrium. Device 100 may be a two magnet vibrating densitometer such as described in U.S. Pat. No. 6,688,176 to Pelletier et al., and assigned to the assignee of the present disclosure.

Flow tube 106 is preferably straight, as this reduces any tendencies for plugging and erosion by materials passing through flow tube 106. However, it is recognized that bent tubes of various shapes, including "U"-shaped tubes, may provide greater measurement sensitivities.

As described above, attached to flow tube 106 are first magnet 108 having first coil 110 wound thereon and second magnet 112 having second coil 114 wound thereon. First magnet 108 and first coil 110 correspond to a vibration detector of device 100 and second magnet 112 and second coil 114 correspond to a vibration source of device 100. Although the vibration source and vibration detector may be located side by side as shown in FIG. 1 the vibration source and vibration detector may be located on opposite sides of flow tube 106 at a point half way between the bulkheads 104 or in other configurations.

As shown in FIG. 1, second coil 114 is coupled to current source 120, which may be an alternating current source. Application of an alternating current from current source 120 to second coil 114 generates an electromagnetic force that interacts with second magnet 112 and causes flow tube 106 to vibrate. First coil 110 is coupled to measurement circuitry 118, wherein the vibration in flow tube 106 moves first magnet 112 within first coil 110, therefore creating a voltage that is provided to measurement circuitry 118. From the provided voltages, measurement circuitry 118 calculates a fluid density of the fluid in flow tube 106.

Figure 2:
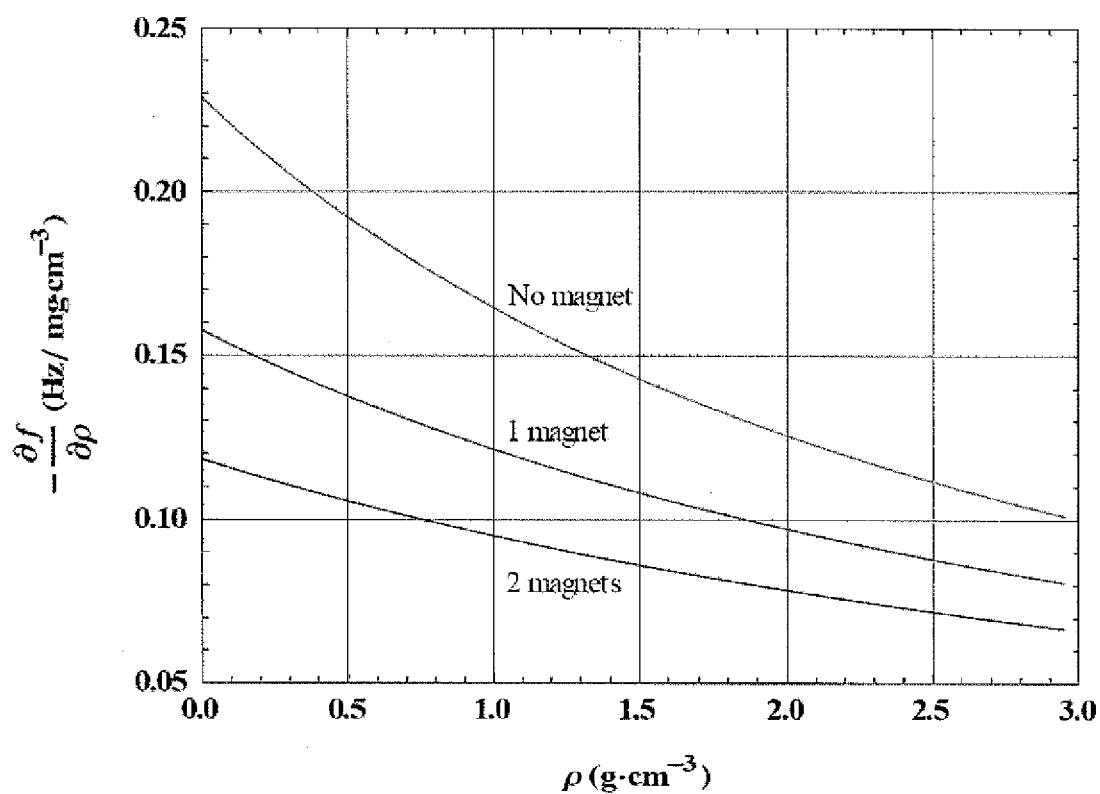
FIG. 2 is a graph illustrating a sensitivity of a device for measuring a density of a fluid having two magnets attached to the flow tube, one magnet attached to the flow tube, and no magnets attached to the flow tube.

However, the use of two magnet-coil arrangements as shown in FIG. 1 has decreased sensitivity due to the two magnets being attached to the flow tube. FIG. 2 is a graph illustrating a sensitivity of a device for measuring a density of a fluid having two magnets attached to the flow tube, one magnet attached to the flow tube, and no magnets attached to the flow tube. As shown in FIG. 2, the removal of one of the magnets from device 100 improves the sensitivity of device 100 by about 25%. Moreover, the removal of both magnets improves the sensitivity of device 100 by about 80%. Further, the removal of one of the magnets from device 100 allows for a magnet-coil combination to be placed at the exact center of flow tube 106. Placing the magnet-coil combination at the center of flow tube 106 drastically reduces the complexity of the calculations and modeling needed to analyze the provided voltages and determine a fluid density. Indeed, the expression for determining the frequency, and from the frequency the density, for device 100 has more than one thousand terms of transcendental functions. Removing one magnet and moving the remaining magnet-coil combination to the center provides a new expression which is less than twenty terms long. Consequently, using a single magnet-coil arrangement may provide not only greater sensitivity for determining a density of a fluid, but also be more useful in environments where computing power is limited, such as downhole environments.

Figure 3:
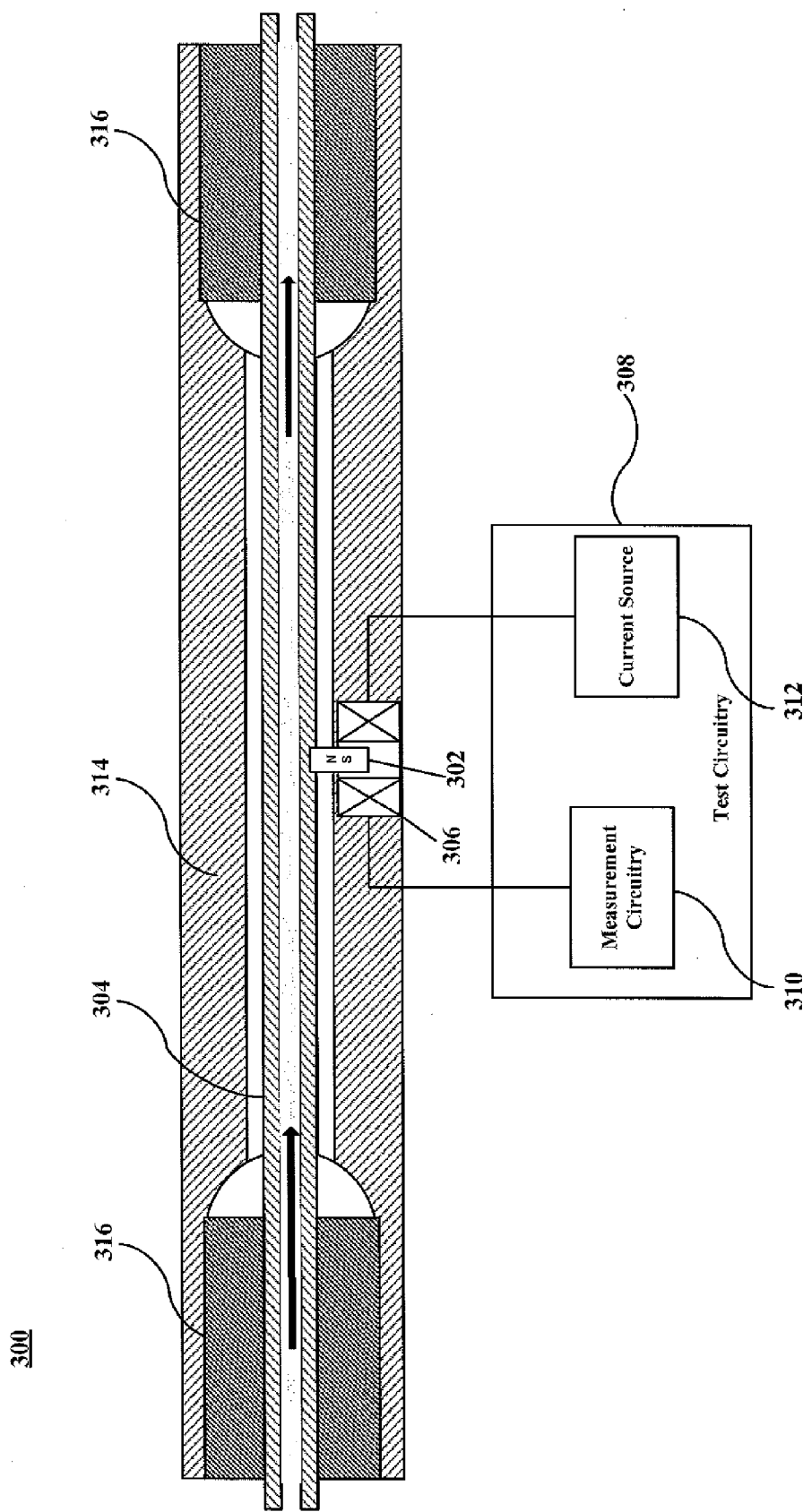
FIG. 3 is a device for measuring a density of a fluid according to some embodiments.

FIG. 3 is a device for measuring a density of a fluid according to some embodiments. As shown in FIG. 3, device 300 includes only a single magnet 302 coupled to flow tube 304. Consistent with some embodiments, single magnet 302 may be mounted on flow tube 304, and in other embodiments, single magnet 302 may be spaced a predetermined distance away from flow tube 304. At least one coil 306 is wound around single magnet 302. As shown in FIG. 3, at least one coil 306 comprises a single coil, however, consistent with other embodiments, at least one coil 306 may include a plurality of coils such as two coils wound around single magnet 302 in a differential arrangement. At least one coil 306 is coupled to test circuitry 308, which includes measurement circuitry 310 and current source 312. Consistent with some embodiments, current source 312 provides a current pulse to at least one coil 306. In other embodiments, current source 312 may be a direct current or alternating current source and provide a direct or alternating steady-state current to at least one coil 306.

Device 300 also includes a rigid housing 314 and two bulkheads 316, similar to device 100 shown in FIG. 1. Rigid housing 314 surrounds and protects a volume through which flow tube 304 passes and reduces the response to vibrations not associated with particular vibratory modes of flow tube 304. Bulkheads 316 seal the volume and secure flow tube 304 within that volume. The volume preferably contains air, a vacuum or a relatively inert gas such as nitrogen or argon. If gasses are used, then they are preferably at atmospheric pressure when the device is at room temperature. Rigid housing 314, bulkheads 316, and flow tube 304 are preferably made from material in a configuration that can withstand pressures of more than 20,000 psi (pounds per square inch) at temperatures of 250° C. or more. Two examples of suitable materials are Titanium and Hastaloy-HA276C. Preferably, bulkheads 316 and flow tube 304 are constructed from the same piece of material, with bulkheads 316 being regions of larger diameter on either end of flow tube 304. Alternatively, flow tube 304 may be welded to bulkheads 316, or otherwise attached. Preferably, rigid housing 314, bulkheads 316, and flow tube 304 are constructed from the same material in order to alleviate thermally induced stresses when the system is in thermal equilibrium.

Consistent with some embodiments, single magnet 302 and at least one coil 306 act as both a vibration source and a vibration detector. Application of a current pulse from current source 312 to at least one coil 306 generates an electromagnetic force that interacts with single magnet 302 and causes flow tube 304 to vibrate. After the current pulse has been applied, the vibration in flow tube 304 moves single magnet 302 within at least one coil 306, therefore creating a voltage on at least one coil 306. At least one coil 306 detects this voltage as it varies over time and provides the detected voltages to measurement circuitry 310. From the provided voltages, measurement circuitry 310 calculates a fluid density of the fluid in flow tube 304. In some embodiments measurement circuitry 310 performs an operation on the provided voltages and determines a resonance frequency of flow tube 304 from the resonance frequency. Consistent with some embodiments, the operations may include a transform which transforms a time-based voltage function representing the voltage induced in at least one coil 306 over time to a frequency based function. The transform may be any known transform such as a discrete Fourier transform (DFT), a fast Fourier transform (FFT), or a discrete wavelet transform. The fluid density of the fluid flowing in flow tube 304 can then be calculated from the determined resonance frequency.

Further consistent with some embodiments, measurement circuitry 310 may include a spectral analyzer configured to perform a specific transform on the time-based voltage function. Alternatively, measurement circuitry 310 may include a processor configured to execute instructions stored in a memory coupled to the processor to perform a specific transform on the time-based voltage function and then execute further instructions stored in the memory to calculate a fluid density from a resonance frequency determined from the specific transform. As yet another alternative, measurement circuitry 310 may include application specific circuitry configured to perform a specific transform, determine a resonance frequency, and then determine a fluid density from the determined resonance frequency. Furthermore, measurement circuitry 310 may also include components capable of calculating further properties of the fluid, such as viscosity of the fluid.

For example, the motion of flow tube 304 as it vibrates may be described by the following equation:

$$(m_T + m_L)\frac{\partial^2 \psi}{\partial t^2} = -EI\frac{\partial^4 \psi}{\partial x^4} + f_P + f_T + f_C + f_V + f_M, \quad (1)$$

where t is time, $\psi$ is a transverse displacement of an element on flow tube 304, x is a distance of the element from one end of flow tube 304, E is an elastic modulus of flow tube 304, I is an area moment of inertia of flow tube 304, $m_L$ is a linear density of the fluid inside flow tube 304, $m_T$ is a linear density of material used to form flow tube 304, $f_P$ is force on flow tube 304 due to pressure, $f_T$ is additional tensile forces on flow tube 304, $f_C$ is the Coriolis force, $f_V$ is a force on flow tube 304 due to fluid flow, and $f_M$ is an additional mass loading due to the presence of magnet 302. From detailed force analysis, it can be shown that the forces are given by:

$$f_P = -PA\frac{\partial^2 \psi}{\partial x^2}, \quad (2)$$

$$f_T = T\frac{\partial^2 \psi}{\partial x^2}, \quad (3)$$

$$f_C = -2m_L V\frac{\partial^2 \psi}{\partial t \partial x}, \quad (4)$$

$$f_V = -m_L V^2 \frac{\partial^2 \psi}{\partial t \partial x}, \quad (5)$$

$$f_M = M\frac{\partial^2 \psi}{\partial t^2}\delta(x - x_1), \quad (6)$$

where T is a tension in flow tube 304, V is a flow velocity of the fluid in flow tube 104, M is the mass of magnet 302, $x_1$ is a location of magnet 302 on flow tube 304, and $\delta(x-x_1)$ is a Dirac delta-functions at $x_1$. When temperature, pressure, and fluid density are known, the differential equation can be solved to yield the wave number $\beta_0$ that is related to the resonance frequency $f_0$ of the flow tube 104 as a function of fluid density:

$$f_0(\rho) = \frac{\beta_0^2}{2\pi L^2}\sqrt{\frac{E(T_t) \cdot I(T_t)}{m_t + m_f}}. \quad (7)$$

This equation may then by inverted to obtain a relationship of the density of the fluid in flow tube 304 as a function of the resonance frequency $f_0$ of the flow tube 304. Consistent with some embodiments, measurement circuitry 310 may apply the above equations to determine a resonance frequency, and then determine a fluid density from the determined resonance frequency.

As shown in FIG. 3, single magnet 302 and at least one coil 304 are positioned along flow tube 304 such that single magnet 302 is mounted on flow tube 304 at a center position along the length of flow tube 304. However, in some embodiments, single magnet 302 may be mounted on or arranged to be coupled to flow tube 304 at other points along the length of flow tube 304. In such embodiments, it is preferable that single magnet 302 and at least one coil 306 be mounted near an antinode (point of maximum displacement from the equilibrium position) of the mode of vibration they are intended to excite and monitor. It is contemplated that more than one mode of vibration may be employed (e.g. the vibration source may switch between multiple frequencies to obtain information from higher resonance harmonic frequencies). The vibration sources and detectors are preferably positioned so as to be near antinodes for each of the vibration modes of interest. The locations of nodes (points of zero vibrational amplitude) and antinodes are determined by the wavelength of the vibration mode and by the mounting of flow tube 304. The frequency f and wavelength $\lambda$ are related to the speed of sound v in the material by the equation $v=f\lambda$.

Figure 4:
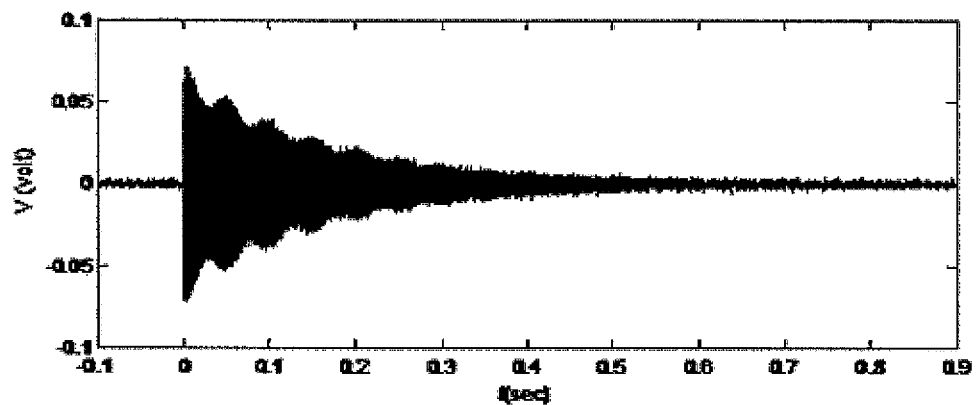
FIG. 4 is a graph illustrating a waveform of a voltage detected as the flow tube vibrates over time.

FIG. 4 is a graph illustrating a waveform of a voltage detected as the flow tube vibrates over time. As shown in FIG. 4, at t=0, at least one coil 306 is modeled as a single coil, and is excited with a current pulse which produces an electromagnetic field to be produced by at least one coil 306 that causes flow tube 304 to vibrate. As flow tube 304 vibrates, a magnetic field produced by single magnet 302 fluctuates as it moves within at least one coil 306. The fluctuating magnetic field produces a voltage in at least one coil 306 which, as shown in FIG. 4, decays over time. This voltage is then provided to measurement circuitry 310 to determine, among other parameters, a resonant frequency of flow tube 304.

Moreover, as shown in FIG. 4, the voltage decays over time. The rate of decay can be determined by measurement circuitry 310 to further determine a Q-factor of the at least one coil 306 vibration detector. The Q-factor of the single coil 306 vibration detector is directly related to the viscosity of the fluid in flow tube 304. Consequently, by determining a Q-factor for the vibration detector, the viscosity of the fluid flowing in flow tube 304.

Figure 5:
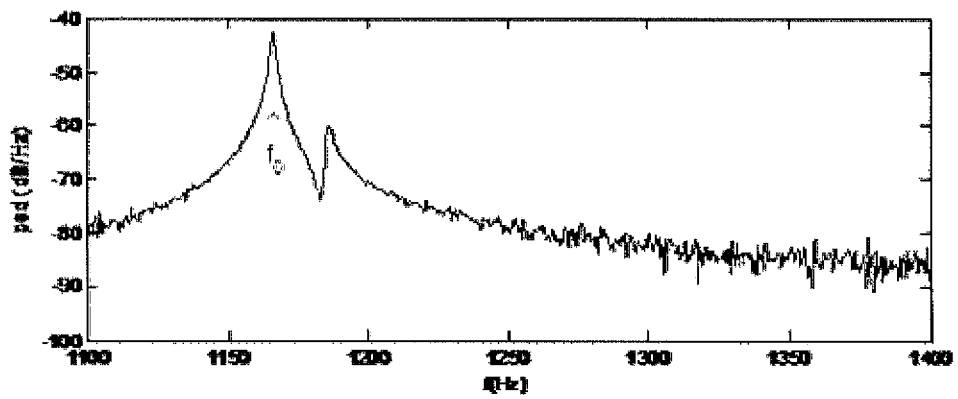
FIG. 5 is a graph showing a calculated signal power spectral density from the detected voltage shown in FIG. 4.

FIG. 5 is a graph shown a calculated signal power spectral density from the detected voltage shown in FIG. 4. Consistent with some embodiments, the signal power spectral density is calculated using a transform which transforms the time-based voltage function shown in FIG. 4 to a frequency based function, such as shown in FIG. 5. The transform may be any known transform such as a discrete Fourier transform (DFT), a fast Fourier transform (FFT), or a discrete wavelet transform. As shown in FIG. 5, a transform of the time-based voltage function produces a graph of frequency versus signal strength wherein the resonant frequency of flow tube 304 will correspond to the strongest peak of the function. For example, for the voltage waveform shown in FIG. 4, the resonant frequency is shown in FIG. 5 as being approximately 1165 Hz.

Figure 6:
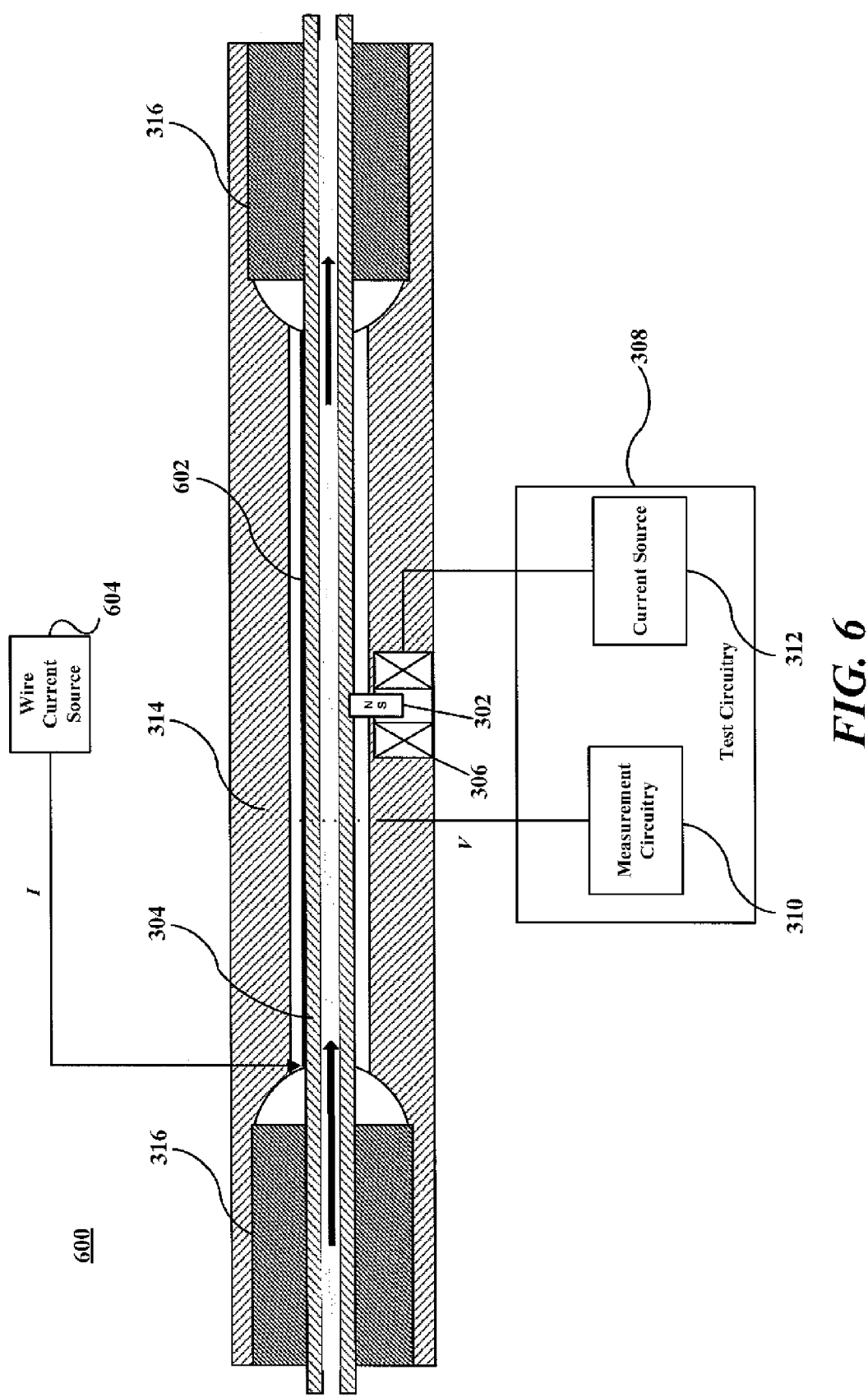
FIG. 6 is a device for measuring a density of a fluid according to some embodiments.

FIG. 6 is a device for measuring a density of a fluid according to some embodiments. Device 600 shown in FIG. 6 is similar to device 300 shown in FIG. 3, so elements which remain the same will not be discussed in detail. However, device 600 differs from device 300 in that metallic wire 602 is used as a vibration detector. Consistent with some embodiments, metallic wire 602 may be a fine metallic wire made of platinum or copper. In operation, a known current I is applied to metallic wire 602 from wire current source 604 that produces a voltage V in metallic wire 602 based on a resistance R of metallic wire. As flow tube 304 vibrates, it also bends, which creates mechanical stress along the length of flow tube 304. This created mechanical stress produces variations in resistance R of metallic wire 602 which, according to Ohm's Law, will also create voltage variations in metallic wire 602. The voltage variations are detected by measurement circuitry 310 and used to calculate a resonance frequency in the same way as discussed above with respect to FIGS. 3-5. Further, as discussed above with respect to FIG. 4, measurement circuitry 310 can further analyze the temporal decay rate of the voltage to determine a Q-factor of the metallic wire 602 vibration detector. Then, the determined Q-factor can be used to determine viscosity of the fluid flowing in flow tube 304.

Figure 7:
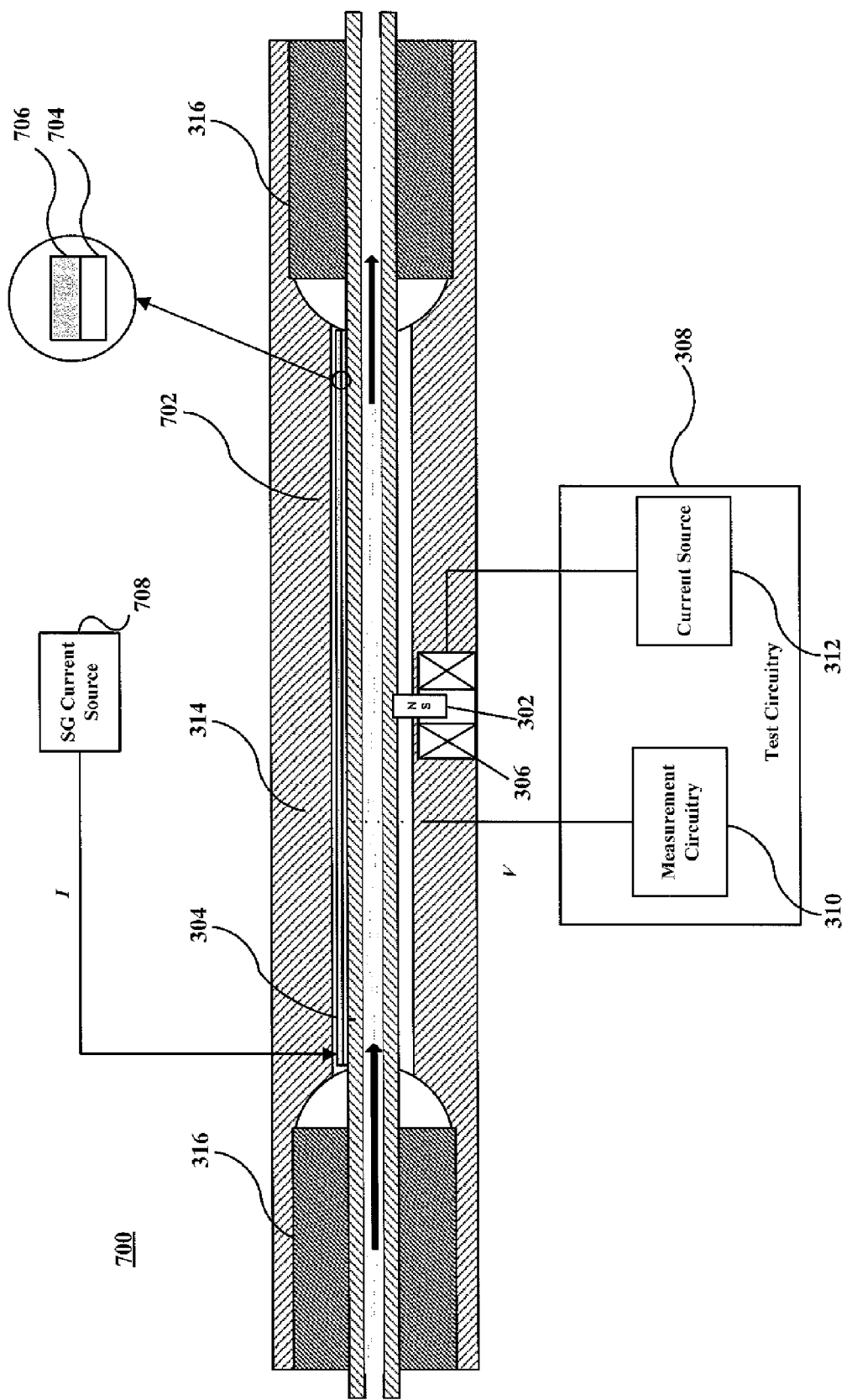
FIG. 7 is a device for measuring a density of a fluid according to some embodiments.

FIG. 7 is a device for measuring a density of a fluid according to some embodiments. Device 700 shown in FIG. 7 is similar to device 600 shown in FIG. 6, so elements that remain the same will not be discussed in detail. However, device 700 differs from device 600 in that strain gauge 702 is used as a vibration detector. Consistent with some embodiments, strain gauge 702 may be an insulator material 704 deposited along a length of flow tube 304 and a metallic or semiconducting material 706 deposited over insulator material 704. Insulator material 704 and metallic or semiconducting material 706 may be deposited on flow tube 304 using known deposition methods. In operation, a known current I is applied to strain gauge 702 from strain gauge current source 708 that produces a voltage V in metallic or semiconductor material 706 based on a resistance R of metallic or semiconductor material 706. As flow tube 304 vibrates, it also bends which creates mechanical stress along the length of flow tube 304. This created mechanical stress produces variations in resistance R of strain gauge 702 that, according to Ohm's Law, will also create voltage variations in metallic or semiconductor material 706. The voltage variations are detected by measurement circuitry 310 and used to calculate a resonance frequency in the same way as discussed above with respect to FIGS. 3-5. Further, as discussed above with respect to FIG. 4, measurement circuitry 310 can further analyze the temporal decay rate of the voltage to determine a Q-factor of the strain gauge 702 vibration detector. Then, the determined Q-factor can be used to determine viscosity of the fluid flowing in flow tube 304.

Figure 8:
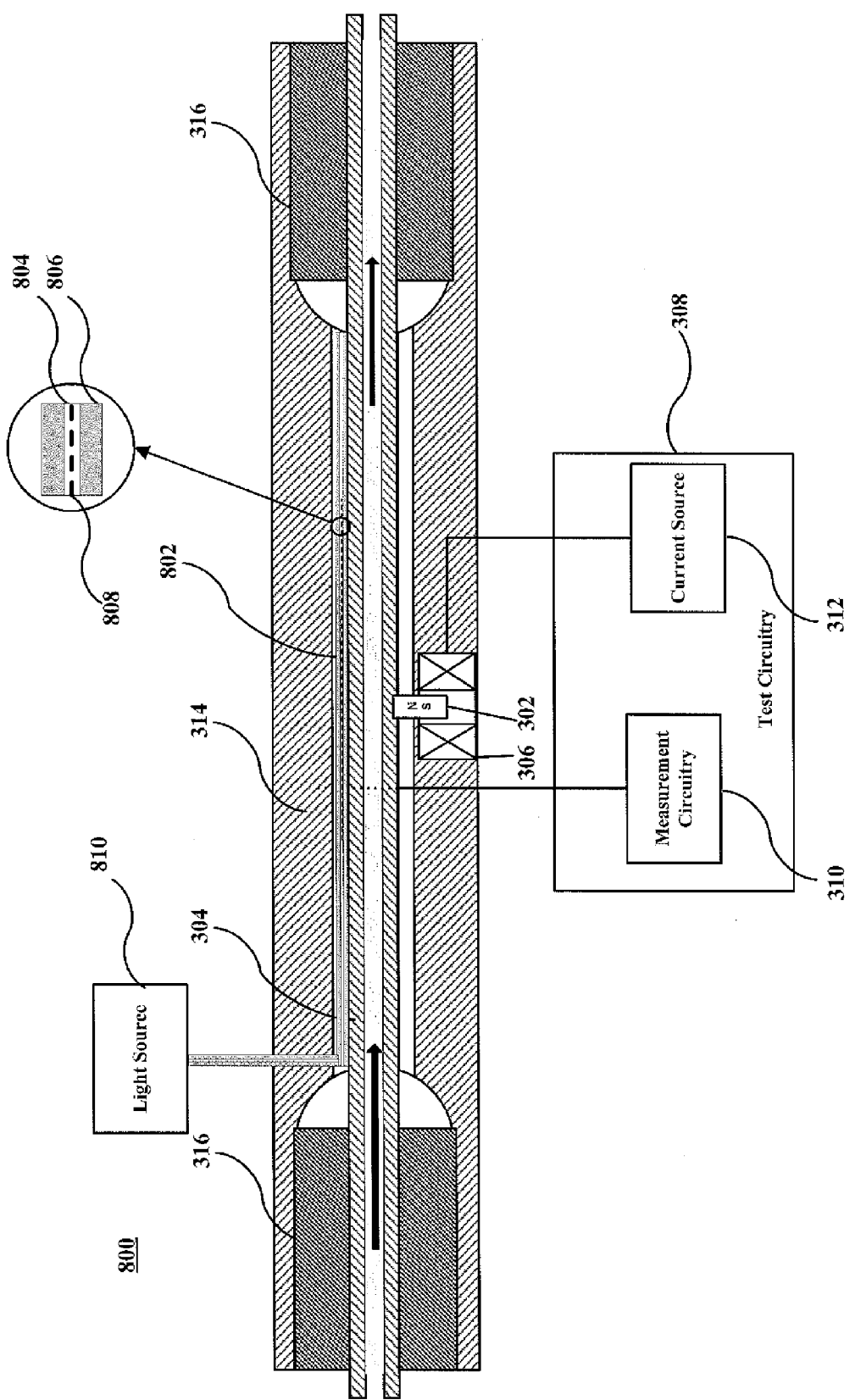
FIG. 8 is a device for measuring a density of a fluid according to some embodiments.

FIG. 8 is a device for measuring a density of a fluid according to some embodiments. Device 800 shown in FIG. 8 is similar to device 600 shown in FIG. 6, so elements which remain the same will not be discussed in detail. However, device 800 differs from device 600 in that fiber optic sensor 802 is used as a vibration detector. Consistent with some embodiments, fiber optic sensor 802 may be a fiber Bragg grating, which includes the fiber optic core 804 surrounded by the fiber optic cladding material 806 with a Bragg grating 808 enclosed in a portion of fiber optic core 804. Bragg grating 808 acts as a period or aperiodic perturbation of the effective refractive index in fiber optic core 804. The refractive index perturbation results in a reflection of light propagating through fiber optic sensor 802 from light source 810 in a narrow range of wavelengths, for which a Bragg condition is satisfied:

$$\frac{2\pi}{\Lambda} = 2\frac{2\pi\eta_{eff}}{\lambda} \Rightarrow \lambda = 2\eta_{eff}\Lambda,$$

where $\Lambda$ is the grating period, $\lambda$ is the vacuum wavelength, and $\Lambda_{eff}$ is the effective refractive index of light in fiber optic sensor 802. The wavelength $\lambda$ of maximum reflectivity (or Bragg wavelength) depends on the grating period $\Lambda$ as well as temperature and mechanical strain, as both of these factors influence the effective refractive index $\eta_{eff}$ of Bragg grating 808 and thus produce changes in the light that is transmitted through or reflected back in fiber optic sensor 802. As flow tube 304 vibrates, it also bends which creates mechanical stress along the length of flow tube 304. This created mechanical stress will influence the effective refractive index $\eta_{eff}$ of Bragg grating 808 and thus produce changes in the light that is transmitted through fiber optic sensor 802. Consequently, measurement circuitry 310 may include an optical sensor that is able to detect these changes and use the changes of light to determine the mechanical stress of flow tube 304 from the vibration of flow tube 304 to determine a resonance frequency of flow tube 304 in a manner similar to that discussed above with respect to FIGS. 3-5. The density of the fluid flowing through flow tube 304 may then be determined from the determined resonance frequency. Further, as discussed above with respect to FIG. 4, measurement circuitry 310 can further analyze the temporal decay rate of the voltage to determine a Q-factor of the fiber optic sensor 802. Then, the determined Q-factor can be used to determine viscosity of the fluid flowing in flow tube 304.

Figure 9:
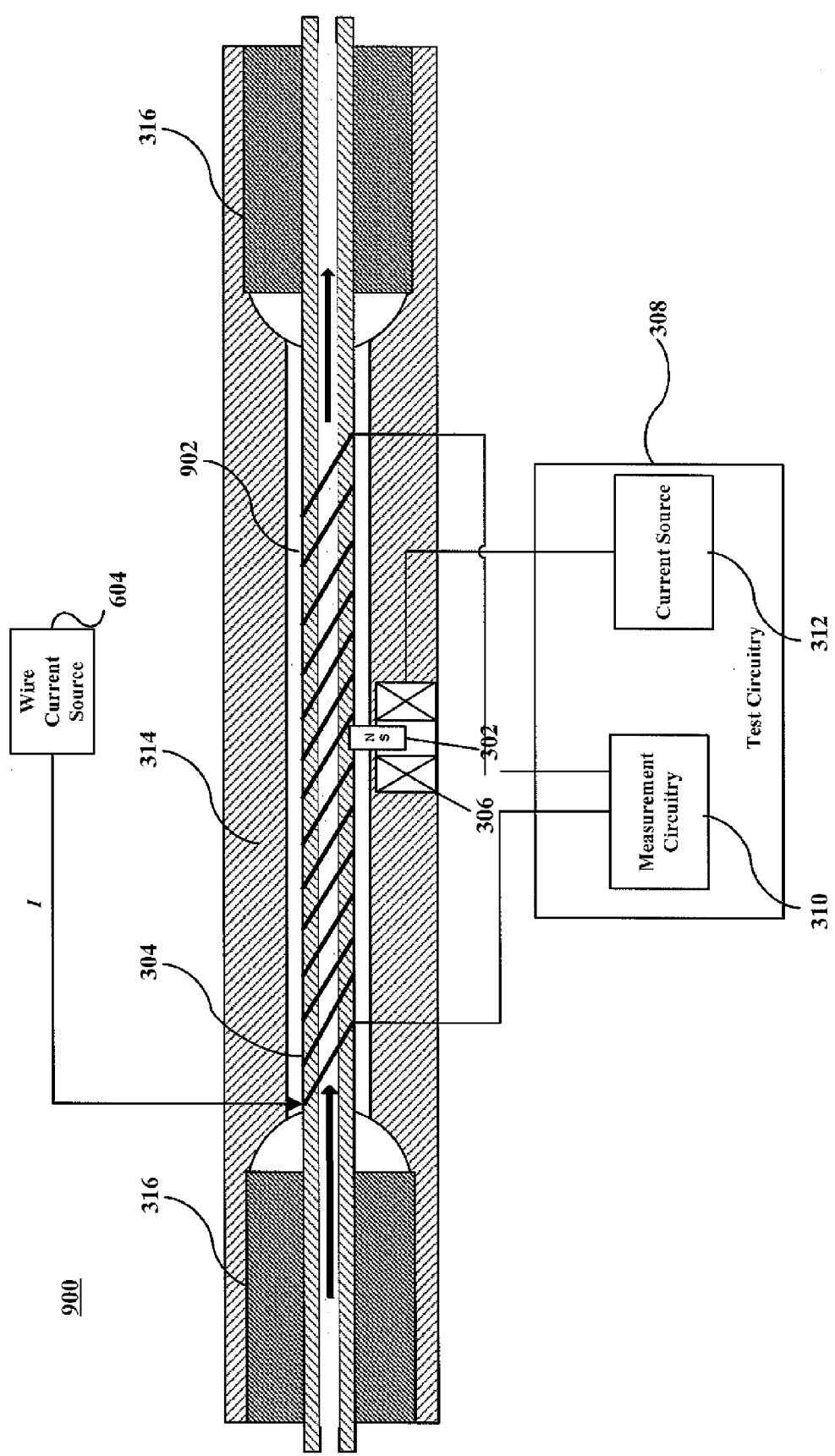
FIG. 9 is a device for measuring a density of a fluid according to some embodiments.

FIG. 9 is a device for measuring a density of a fluid according to some embodiments. Device 900 shown in FIG. 9 is similar to device 600 shown in FIG. 6, so elements that remain the same will not be discussed in detail. However, device 900 differs from device 600 in that strain gauge metallic wire 602 is wrapped around flow tube 304. Consistent with some embodiments, metallic wire 602 may be a fine metallic wire made of platinum or copper. In other embodiments, strain gauge 702 or fiber optic sensor 802 may be substituted for metallic wire 602 and be wrapped around flow tube 304. In operation, a known current I is applied to metallic wire 602 from wire current source 604, which produces a voltage V in metallic wire 602 based on a resistance R of metallic wire. As flow tube 304 vibrates, it also bends which creates mechanical stress along the length of flow tube 304. This created mechanical stress produces variations in resistance R of metallic wire 602 that, according to Ohm's Law, will also create voltage variations in metallic wire 602. The voltage variations are detected by measurement circuitry 310 and used to calculate a resonance frequency in the same way as discussed above with respect to FIGS. 3-5. Further, as discussed above with respect to FIG. 4, measurement circuitry 310 can further analyze the temporal decay rate of the voltage to determine a Q-factor of the metallic wire 602 vibration detector. Then, the determined Q-factor can be used to determine viscosity of the fluid flowing in flow tube 304.

Consistent with some embodiments, using metallic wire 602 (or strain gauge 702 or optic sensor 802) wrapped around flow tube 304, the hoop stress of flow tube 304 may be determined. Under a pressure P, a flow tube such as flow tube 304, with inner radius b and outer radius a will experience expansion in its outer radius by $$\Delta a = \frac{Pb^2(2-\nu)}{E(a^2-b^2)}, \quad (10)$$

where E is the elastic modulus of flow tube 304, and ν is the Poisson's ratio of flow tube 304. The change in radius Δa results in a change in the outer circumference (2πa) of the tube which in turn results in minute change in the resistance R of metallic wire 602 wrapped around flow tube 304. This resistance change ΔR may then be measured using well known methods, such as using a quarter-bridge Wheatstone bridge composed of metallic wire 602 and three dummy resistors and excited by a voltage $V_{br}$, such that the strain ε from pressure P may be determined by $$\varepsilon = \frac{\Delta R}{SR},$$

where S is a strain sensitivity factor determined by the material of metallic wire 602. Because the strain ε may be equal to $$\frac{\Delta a}{a},$$

knowing the strain ε from pressure P and the change in radius Δa, the pressure P from the fluid in flow tube 304 can be determined using equation (10). Once the pressure P is determined, measurement circuitry 310 may then determine the hoop stress $\sigma_\theta$ of flow tube 304 using the equation $$\sigma_\theta = \frac{P \cdot r}{t},$$

where P is the internal pressure from the fluid, t is the thickness of the wall of flow tube 304, and r is the radius of flow tube 304.

Figure 10:
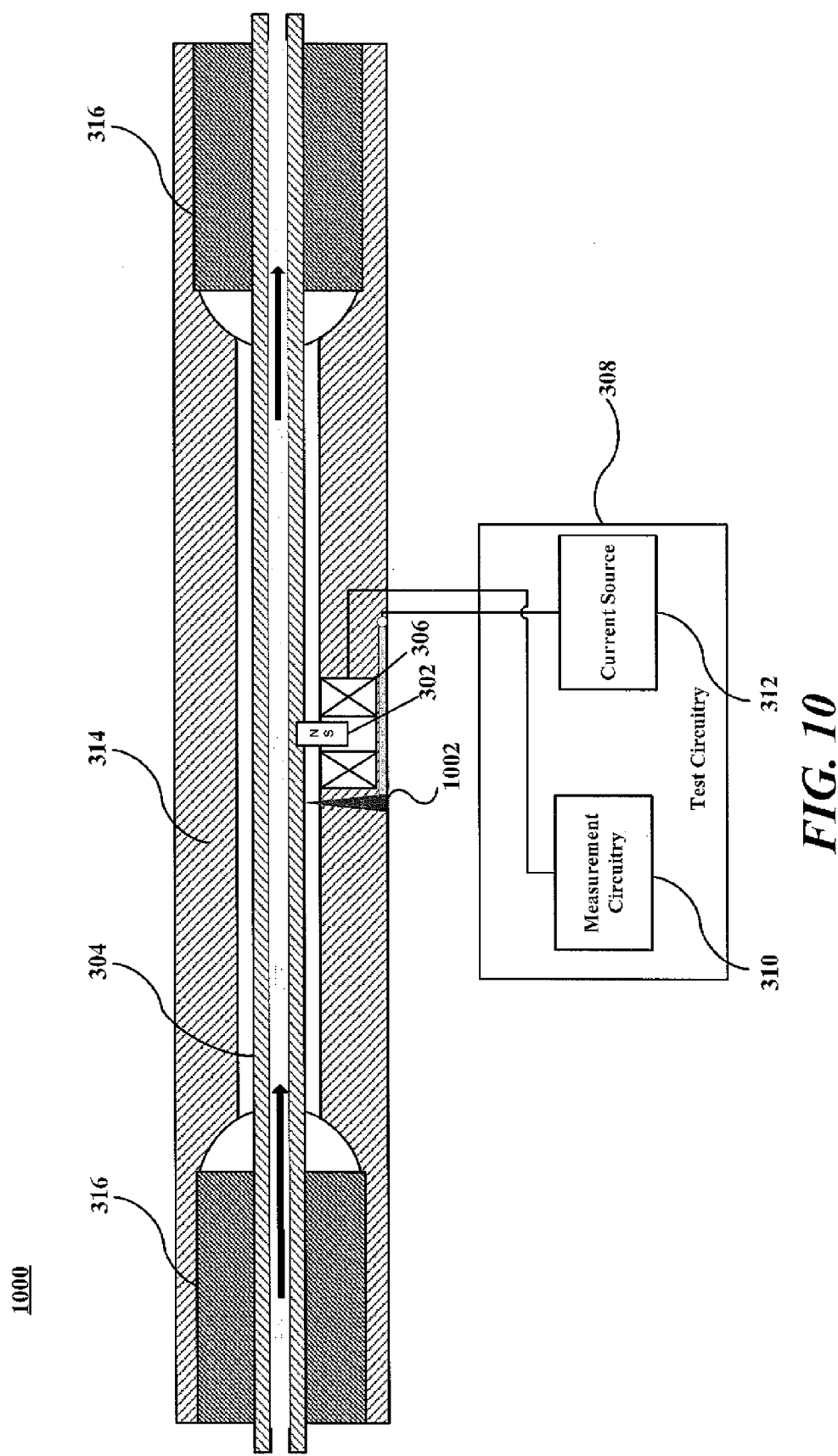
FIG. 10 is a device for measuring a density of a fluid according to some embodiments.

FIG. 10 is a device for measuring a density of a fluid according to some embodiments. Device 1000 shown in FIG. 10 is similar to device 300 shown in FIG. 3, so elements that remain the same will not be discussed in detail. However, device 1000 differs from device 300 in that electric hammer 1002 is used as a vibration source. As shown in FIG. 10, single magnet 302 is spaced away from flow tube 304 by a predetermined amount such that single magnet 302 is not mounted on flow tube 304. Referring back to FIG. 2, removing single magnet 302 from flow tube 304 such that no magnets are mounted on flow tube 304 may provide a sensitivity increase of almost 80% when compared with the two magnet embodiment shown in FIG. 1.

In operation, current source 312 is coupled to electric hammer 1002 and is capable of providing a current pulse to electric hammer 1002 causing electric hammer 1002 to strike flow tube 304 such that flow tube 304 vibrates. After the current pulse has been applied, the vibration in flow tube 304 moves single magnet 302 within at least one coil 306, therefore creating a voltage. At least one coil 306 detects this voltage as it varies over time and provides the detected voltages to measurement circuitry 310. From the provided voltages, measurement circuitry 310 calculates a fluid density of the fluid in flow tube 304, as described above with respect to FIGS. 4 and 5. Further, as discussed above with respect to FIG. 4, measurement circuitry 310 can further analyze the temporal decay rate of the voltage to determine a Q-factor of the single coil vibration detector. Because the viscosity of a fluid influences the Q-factor of a vibratory device, the determined Q-factor can be used to determine viscosity of the fluid flowing in flow tube 304.

Figure 11:
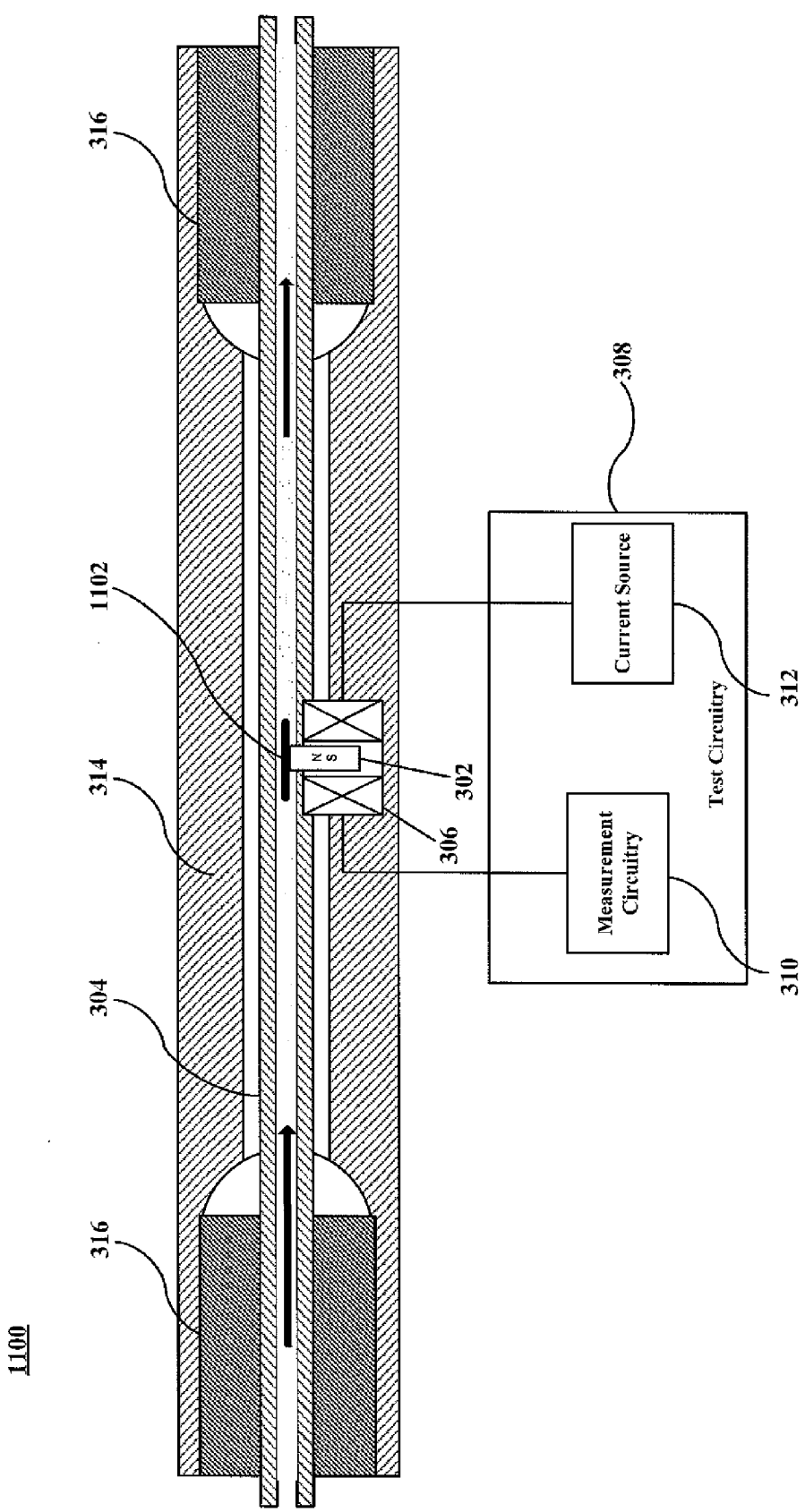
FIG. 11 is a device for measuring a density of a fluid according to some embodiments.

FIG. 11 is a device for measuring a density of a fluid according to some embodiments. Device 1100 shown in FIG. 11 is similar to device 300 shown in FIG. 3, so elements which remain the same will not be discussed in detail. However, device 1100 differs from device 300 in that single magnet 302 is attached to a tab 1102 mounted on a side of flow tube 304. Thus, when current source 312 provides a pulse current to at least one coil 306, the electromagnetic field produced by at least one coil 306 interacts with single magnet 302 to cause single magnet 302 to apply a normal force on tab 1102, which applies a torque on flow tube 304, and creates a torsional vibration in flow tube 304. According to some embodiments, electric hammer 1002 may be used as a vibration source instead of single magnet 302 such that electric hammer 1002 strikes tab 1102 to create a torsional vibration in flow tube 304. Using the same principles of operation as device 300, the torsional vibration will cause single magnet 302 to move within at least one coil 306 and create a voltage on at least one coil 306 that is provided to measurement circuitry 312 and can be used to determine a resonance frequency and, thus, a density of the fluid flowing in flow tube 304. Moreover, by monitoring the torsional vibration, the viscosity of the fluid flowing in flow tube 304 can also be determined. This may be done by determining the Q-factor of the torsional vibration which is directly influenced by viscosity, as discussed above. Thus, device 1100 allows for the simultaneous determination of both the density and viscosity of the fluid flowing in flow tube.

Consequently, embodiments described herein provide improvements in the design of fluid densitometers. For example, embodiments described herein use a single magnet and at least one coil mounted on a flow tube, which provides greater sensitivity and over two magnet embodiments. Single magnet and at least one coil embodiments also provide for greater ease in calculating the fluid density based on a monitored vibration of the flow tube. Moreover, single magnet and at least one coil embodiments only require a single magnet to be mounted on the flow tube, providing for ease of construction. Other embodiments disclosed herein may provide greater sensitivity by removing the magnet entirely from the flow tube and instead driving a vibration using an electric hammer Other embodiments use strain gauges, resistant detectors, and optical detection device which allow other properties, such as a fluid viscosity or fluid pressure to be measured along with the fluid density. Furthermore, embodiments as described herein provide a device for measuring a torsional vibration which can be used to determine the fluid viscosity along with the fluid density. Embodiments described herein are exemplary only. One skilled in the art may recognize various alternative embodiments from those specifically disclosed. Those alternative embodiments are also intended to be within the scope of this disclosure. As such, the embodiments are limited only by the following claims.

The invention claimed is:

1. An instrument for measuring fluid properties, comprising:
   a tube, the tube receiving a sample of the fluid;
   a testing module including measurement circuitry and a current source;
   an excitation source coupled to the testing module, the excitation source comprising at least one coil wound around a single magnet, the excitation source being configured to excite the tube into a vibrating state;
   a strain gauge coupled to the tube and coupled to the measurement circuitry; and
   a strain gauge current source coupled to the strain gauge and providing a strain gauge current, wherein:
      a resistance of the strain gauge changes in response to mechanical stress generated along the tube as it vibrates;
      a voltage induced by the strain gauge current varies as the resistance changes; and
      the measurement circuitry measures the varying voltage induced in the strain gauge by the strain gauge current over time to determine the resonance frequency of the tube.

2. The instrument of claim 1, wherein the single magnet is attached to the tube and the at least one coil is coupled to the current source.

3. The instrument of claim 2, wherein the current source provides a current to the at least one coil wound around the single magnet to produce a magnetic field that interacts with the single magnet to excite the tube into the vibrating state.

4. The instrument of claim 3, wherein the single magnet vibrates in the at least one coil as the tube vibrates to generate a voltage in the at least one coil that varies over time, and the varying voltage is detected by the measurement circuitry.

5. The instrument of claim 4, wherein the measurement circuitry performs a transform on the detected voltage to determine a resonance frequency of the tube and determines a density of the fluid from the determined resonance frequency.

6. The instrument of claim 3, further comprising a detector coupled to the measurement circuitry, the detector having a Q-factor and measuring parameters related to the vibration of the tube, wherein:
   the measured parameters are provided to the measurement circuitry to determine a resonance frequency of the tube; and
   a temporal decay rate of the measured parameters is determined by the measurement circuitry to measure the Q-factor of the detector, wherein a viscosity of the fluid can be determined from the measured Q-factor.

7. The instrument of claim 2, wherein the excitation source further comprises:
   an electric hammer coupled to the test circuitry and the tube, the electric hammer receiving a current pulse from the test circuitry and striking the tube to excite the tube into the vibrating state; and
   the single magnet vibrates in the at least one coil as the tube vibrates to generate a voltage in the at least one coil that varies over time, and the varying voltage is detected by the measurement circuitry.

8. The instrument of claim 7, wherein the measurement circuitry performs a transform on the detected voltage to determine a resonance frequency of the tube and determines a density of the fluid from the determined resonance frequency.

9. The instrument of claim 7, wherein the single magnet and at least one coil are spaced away from the tube by a predetermined distance.

10. The instrument of claim 7, further comprising:
    at least one tab attached to a side of the tube, wherein the electric hammer strikes the tab to provide a torsional force on the tube and produce a torsional vibration of the tube.

11. The instrument of claim 1, wherein the strain gauge comprises at least one of a metallic wire lined along a length of the tube, a semiconductor material deposited on the tube.

12. The instrument of claim 1, wherein:
    the strain gauge is wrapped around the tube to measure a hoop stress of the tube; and
    the measurement circuitry determines a pressure of the fluid in the tube from the measured hoop stress.

13. The instrument of claim 1, further comprising:
    at least one tab attached to a side of the tube; and
    the single magnet is attached to the at least one tab, wherein:
       the single magnet interacts with the tab to provide a torsional force on the tube and produce a torsional vibration of the tube.

14. An instrument for determining fluid properties, comprising:
    a tube receiving the fluid;
    a single magnet;
    at least one coil wound around the single magnet, wherein the at least one coil is coupled to a pulse current source and receives a pulse current that creates a magnetic field in the at least one coil, the created magnetic field interacting with the single magnet to excite the tube into a vibrating state; and
    a detector coupled to the tube, wherein:
       the detector is coupled to measurement circuitry and detects properties of the tube as it vibrates, and the measurement circuitry determines the fluid properties based on the detected properties;
       the detector comprises a strain gauge coupled to the tube and coupled to the measurement circuitry, the detector further comprising a strain gauge current source coupled to the strain gauge and providing a strain gauge current,
       a resistance of the strain gauge changes in response to mechanical stress generated along the tube as it vibrates;
       a voltage induced by the strain gauge current varies as the resistance changes; and
       the measurement circuitry measures the varying voltage induced in the strain gauge by the strain gauge current over time to determine the resonance frequency of the tube.

15. The instrument of claim 14, wherein:
the detector comprises the at least one coil wound around the single magnet;
the single magnet vibrates in the at least one coil as the tube vibrates to generate a voltage in the at least one coil that varies over time, and the varying voltage is detected by the measurement circuitry;
the measurement circuitry performs a transform on the detected voltages to determine a resonance frequency of the tube; and
the measurement circuitry determines a density of the fluid from the determined resonance frequency.

16. The instrument of claim 14, wherein the strain gauge comprises at least one of a metallic wire lined along a length of the tube, or a semiconductor material deposited on the tube.

17. The instrument of claim 14, wherein:
the strain gauge is wrapped around the tube to measure a hoop stress of the tube; and
the measurement circuitry determines a pressure of the fluid in the tube from the measured hoop stress.

18. An instrument for measuring fluid properties, comprising:
a tube, the tube receiving a sample of the fluid;
a testing module including measurement circuitry and a current source;
an excitation source coupled to the testing module, the excitation source comprising at least one coil wound around a single magnet, the excitation source being configured to excite the tube into a vibrating state;
an optical fiber coupled to the tube and to the measurement circuitry, the optical fiber comprising a cladding surrounding a core, and a Bragg grating formed in the core; and
a light source coupled to the optical fiber and providing light through the optical fiber, wherein:
properties of the light through the optical fiber change in response to a mechanical stress caused by the vibration of the tube; and
the measurement circuitry detects the changing light properties and determines a resonant frequency and a fluid density.

19. An instrument for measuring fluid properties, comprising:
a tube, the tube receiving a sample of the fluid;
a testing module including measurement circuitry and a current source;
an excitation source coupled to the testing module, the excitation source comprising:
at least one coil wound around a single magnet;
an electric hammer coupled to the testing module and the tube, the electric hammer receiving a current pulse from the test module and striking the tube to excite the tube into the vibrating state; and
the single magnet vibrates in the at least one coil as the tube vibrates to generate a voltage in the at least one coil that varies over time, and the varying voltage is detected by the measurement circuitry.

20. The instrument of claim 19, wherein the measurement circuitry performs a transform on the detected voltage to determine a resonance frequency of the tube and determines a density of the fluid from the determined resonance frequency.

21. The instrument of claim 19, wherein the single magnet and at least one coil are spaced away from the tube by a predetermined distance.

22. The instrument of claim 19, further comprising at least one tab attached to a side of the tube, wherein the electric hammer strikes the tab to provide a torsional force on the tube and produce a torsional vibration of the tube.

* * * * *